(12) United States Patent
Nakashita

(10) Patent No.: US 7,154,020 B2
(45) Date of Patent: Dec. 26, 2006

(54) BODY FLUID ABSORBENT WEARING ARTICLE

(75) Inventor: Masashi Nakashita, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 624 days.

(21) Appl. No.: 10/024,544

(22) Filed: Dec. 21, 2001

(65) Prior Publication Data

US 2002/0082574 A1    Jun. 27, 2002

(30) Foreign Application Priority Data

Dec. 25, 2000   (JP) ............................. 2000-393721

(51) Int. Cl.
*A61F 13/15* (2006.01)
*A61F 13/536* (2006.01)
*B32B 7/02* (2006.01)

(52) U.S. Cl. .............................. 604/380; 604/385.101; 428/218

(58) Field of Classification Search ................ 604/370, 604/372, 374, 378–386, 383, 385.101
See application file for complete search history.

(56) References Cited

U.S. PATENT DOCUMENTS

| | | | | |
|---|---|---|---|---|
| 2,952,260 A | * | 9/1960 | Burgeni | 604/374 |
| 3,017,304 A | * | 1/1962 | Burgeni | 428/167 |
| 3,046,986 A | * | 7/1962 | Harwood | 604/375 |
| 3,494,362 A | * | 2/1970 | Burgeni | 604/374 |
| 3,612,055 A | * | 10/1971 | Mesek et al. | 604/365 |
| 3,858,585 A | * | 1/1975 | Chatterjee | 604/376 |
| 4,027,672 A | | 6/1977 | Karami | |
| 4,397,644 A | | 8/1983 | Matthews et al. | |
| 4,435,178 A | * | 3/1984 | Fitzgerald | 604/365 |
| 4,443,492 A | * | 4/1984 | Roller | 427/501 |
| 4,600,458 A | | 7/1986 | Kramer et al. | |
| 4,676,786 A | | 6/1987 | Nishino | |
| 4,880,419 A | * | 11/1989 | Ness | 604/368 |
| 5,423,786 A | * | 6/1995 | Fung et al. | 604/367 |
| 5,500,270 A | * | 3/1996 | Langdon et al. | 428/119 |
| 5,545,155 A | * | 8/1996 | Hseih et al. | 604/378 |
| 5,941,863 A | * | 8/1999 | Guidotti et al. | 604/378 |
| 5,990,377 A | * | 11/1999 | Chen et al. | 604/381 |
| 6,037,518 A | * | 3/2000 | Guidotti et al. | 604/378 |
| 6,090,994 A | * | 7/2000 | Chen | 604/378 |
| 6,436,082 B1 | * | 8/2002 | Mizutani et al. | 604/385.101 |
| 6,642,432 B1 | * | 11/2003 | Matsui et al. | 604/380 |
| 6,685,686 B1 | * | 2/2004 | Hermansson et al. | 604/385.101 |
| 6,803,334 B1 | * | 10/2004 | Mizutani et al. | 442/394 |

FOREIGN PATENT DOCUMENTS

JP     5-253259     10/1993

* cited by examiner

*Primary Examiner*—Karin Reichle
(74) *Attorney, Agent, or Firm*—Lowe Hauptman & Berner LLP

(57) ABSTRACT

A body fluid absorbent wearing article includes a liquid-absorbent panel. The panel is composed of a first fibrous assembly panel lying on the side of a topsheet and a second fibrous assembly panel underlying the first sub-panel. The first sub-panel has a flat portion, a plurality of protuberant portions and a plurality of wall portions. The first sub-panel has a fiber density that increases toward the second sub-panel which has a fiber density higher than that of the first panel.

2 Claims, 6 Drawing Sheets

BODY FLUID ABSORBENT WEARING ARTICLE

BACKGROUND OF THE INVENTION

This invention relates to a body fluid absorbent wearing article for absorption and containment of body fluids such as a disposable diaper, a sanitary napkin, a liquid-absorbent pad and the like.

Japanese Patent Application Publication No. 1993-253259A discloses a body fluid absorbent wearing article comprising a liquid-pervious topsheet, a liquid-impervious backsheet and a liquid-absorbent panel disposed between these sheets. The panel comprises a first sub-panel facing the topsheet and a substantially nonapertured second sub-panel underlying the first sub-panel. The first sub-panel comprises thermoplastic synthetic resin fiber by 10–70 wt % and cellulose fiber by 30–90 wt %. The cellulose fiber contains therein super-absorptive polymer particles. The first sub-panel has a plurality of through-openings with an opening area of 10–2,000 mm$^2$ and an opening percentage of 2–70 %. The topsheet has a plurality of fine apertures with an opening area of 10–2,000 mm$^2$ and an opening percentage of 2–70 %.

In this article of well known art, solid ingredients of body fluids having passed the fine apertures of the topsheet are received in the through-openings of the first sub-panel liquid ingredients are absorbed in the first and second sub-panels. With this article, it is not concerned that any amount of solid ingredients might stay on the topsheet and the solid ingredients once having been received in the through-openings of the first sub-panel might return back from the panel to the topsheet.

However, the liquid ingredients such an urine, loose passage or menstrual discharge having been absorbed in the first sub-panel over a given area thereof are prevented by the plurality of through-openings from rapidly spreading in the entire first sub-panel.

In addition, this known article includes no particular construction adapted to ensure that the liquid ingredients such as urine, loose passage or menstrual discharge having been absorbed in the first sub-panel can smoothly transfer to the second sub-panel. Consequently, it is impossible for the second sub-panel spaced from the topsheet to positively retain these body fluids. Under the wearer's body weight exerted on the panel, the first and second sub-panels are compressed and these body fluids still staying in the first sub-panel may often flow back to the topsheet.

SUMMARY OF THE INVENTION

It is an object of this invention to provide a body fluid absorbent wearing article improved so that the body fluids may rapidly spread in the absorbent panel over its entire region and be prevented from flowing back to the topsheet.

According to this invention, there is provided a body fluid absorbent wearing article comprising a liquid-pervious topsheet, a liquid-impervious backsheet and a liquid-absorbent panel disposed between these sheets.

The absorbent panel composed of a first fibrous assembly sub-panel lying on a side of the topsheet and having a compressive restoring elasticity and a substantially flat second fibrous assembly sub-panel underlying the first fibrous assembly sub-panel. The first fibrous assembly sub-panel has a substantially flat portion spaced upward from the second fibrous assembly sub-panel by a given dimension and a plurality of protuberant portions embossed on the flat portion toward the second fibrous assembly panel so as to bear against the second fibrous assembly sub-panel. The first fibrous assembly sub-panel has a fiber density progressively increasing toward the second fibrous assembly sub-panel. The second fibrous assembly sub-panel has a fiber assembly higher than that of the first fibrous assembly sub-panel.

This invention includes one embodiment in which the first fibrous assembly sub-panel has a plurality of wall portions each extending from the flat portion toward the second fibrous assembly sub-panel but spaced from the second fibrous assembly sub-panel by a given dimension. Wall portions are provide to connect the adjacent protuberant portions with each other.

This invention includes another embodiment in which the first fibrous assembly sub-panel has a fiber density of 0.03–0.10 g/cm$^3$ in the flat portion and a fiber density of 0.05–0.15 g/cm$^3$ in the protuberant portions as well as in the wall portions, and the second fibrous assembly sub-panel has a fiber density of 0.10–0.50 g/cm$^3$.

This invention includes still another embodiment in which the first fibrous assembly sub-panel comprises hydrophilic thermoplastic synthetic resin fiber by 70–100 wt % and cellulose fiber by 0–30 wt % while the second fibrous assembly sub-panel comprises the synthetic resin fiber by 0–50 wt % and the cellulose fiber by 50–100 wt %.

This invention includes further another embodiment in which the second fibrous assembly sub-panel contains fibrous or granular super-absorptive polymer by 0–50 wt %.

DETAILED DESCRIPTION OF THE PREFERRED EMBODIMENTS

Details of a body fluid absorbent wearing article according to this invention will be more fully understood from the description given hereunder with reference to the accompanying drawings.

Figure 1:
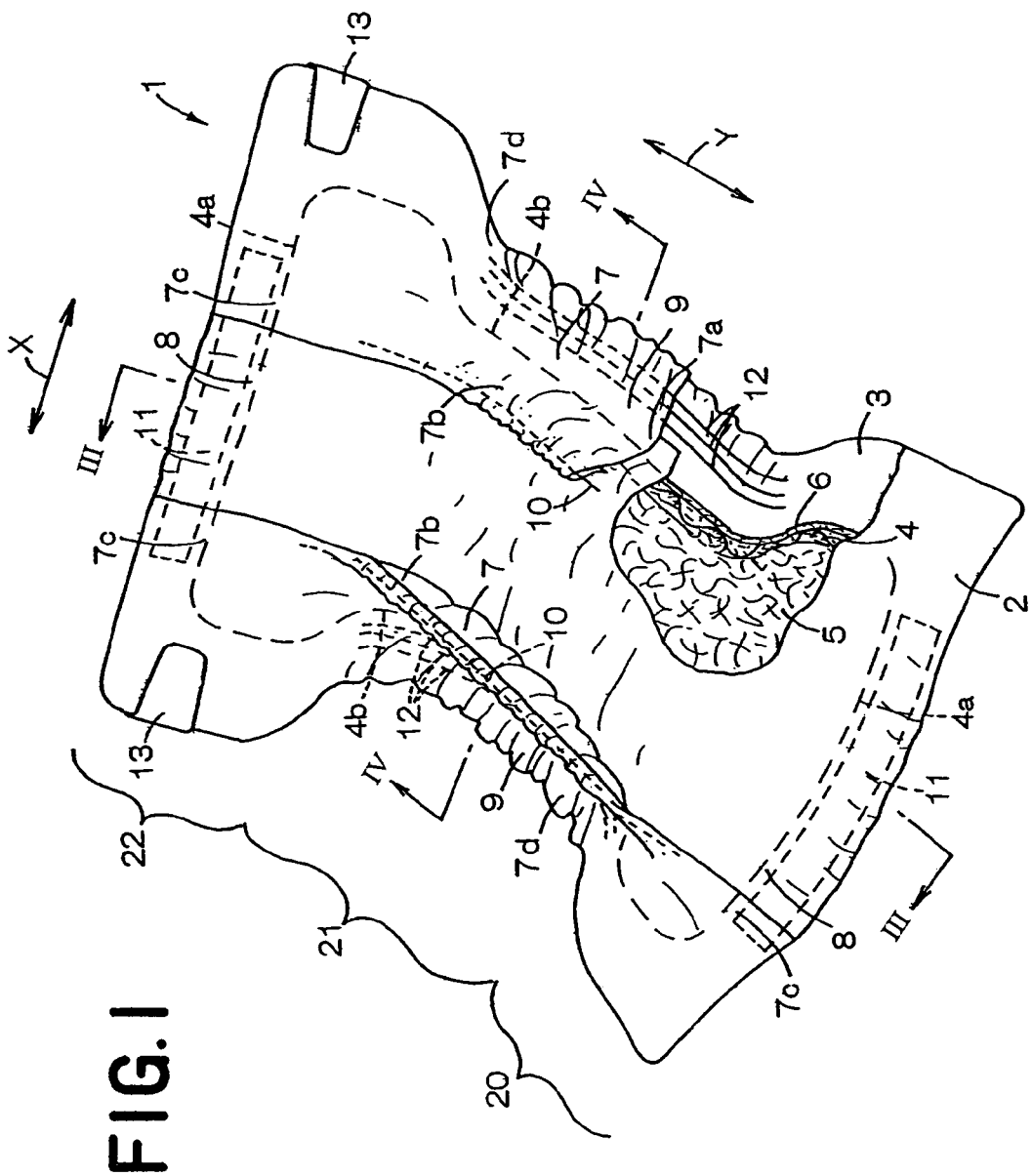
FIG. 1 is partially cutaway perspective view of a diaper as viewed from a side of a topsheet.
Figure 2:
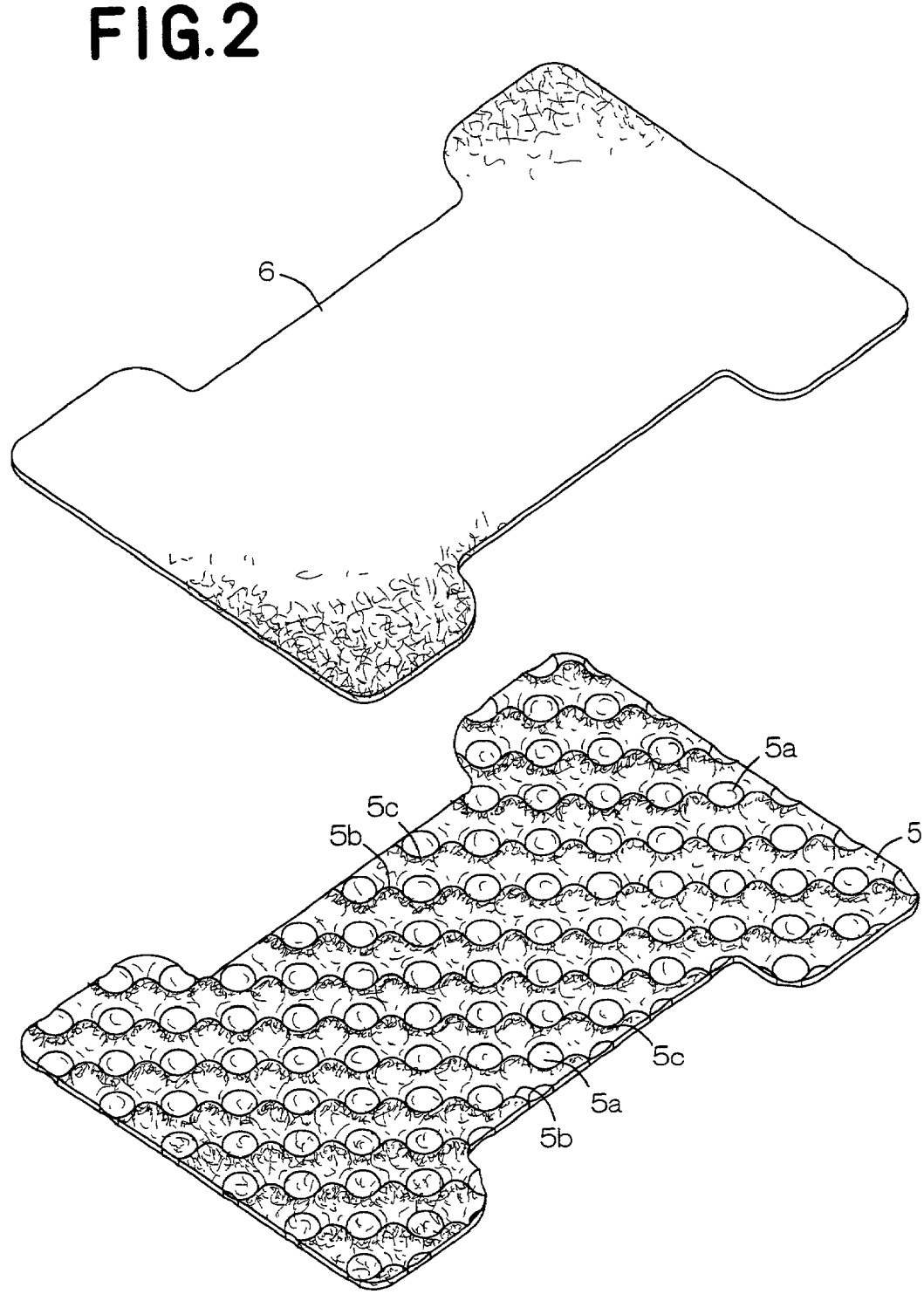
FIG. 2 is perspective view of the first and second sub-panels as separated from each other.
Figure 3:
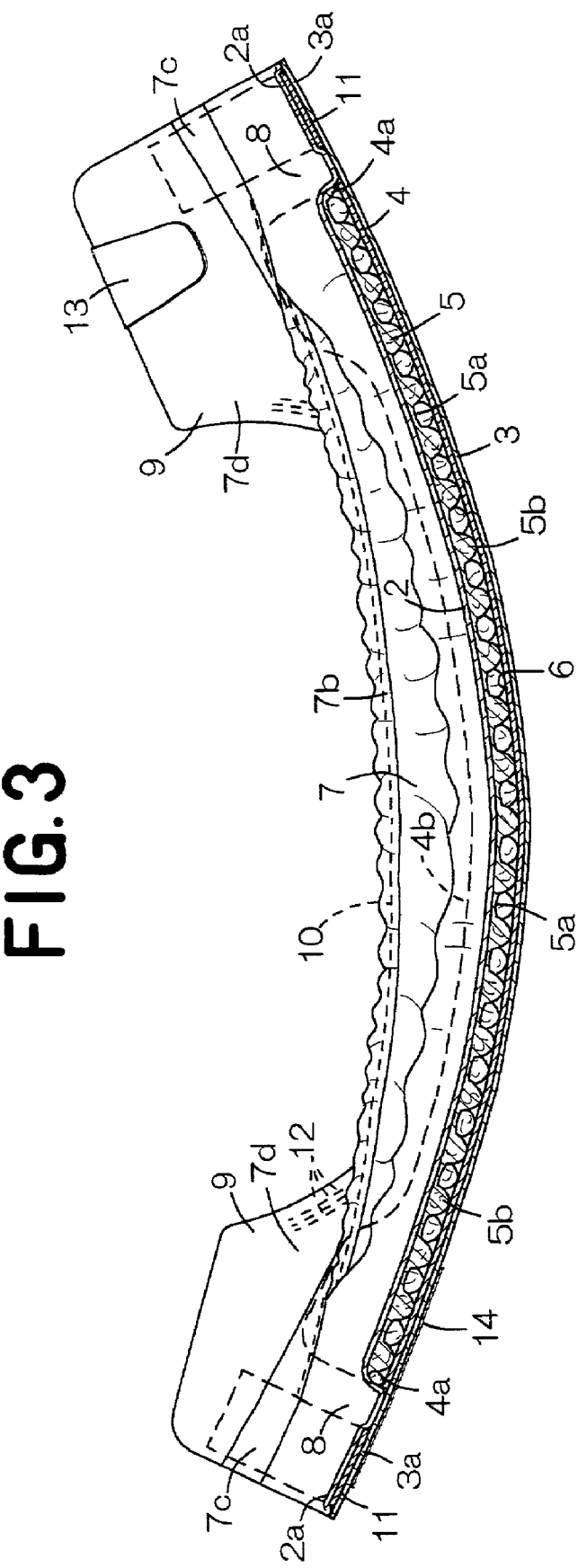
FIG. 3 is sectional view taken along a line III—III in FIG. 1.
Figure 4:
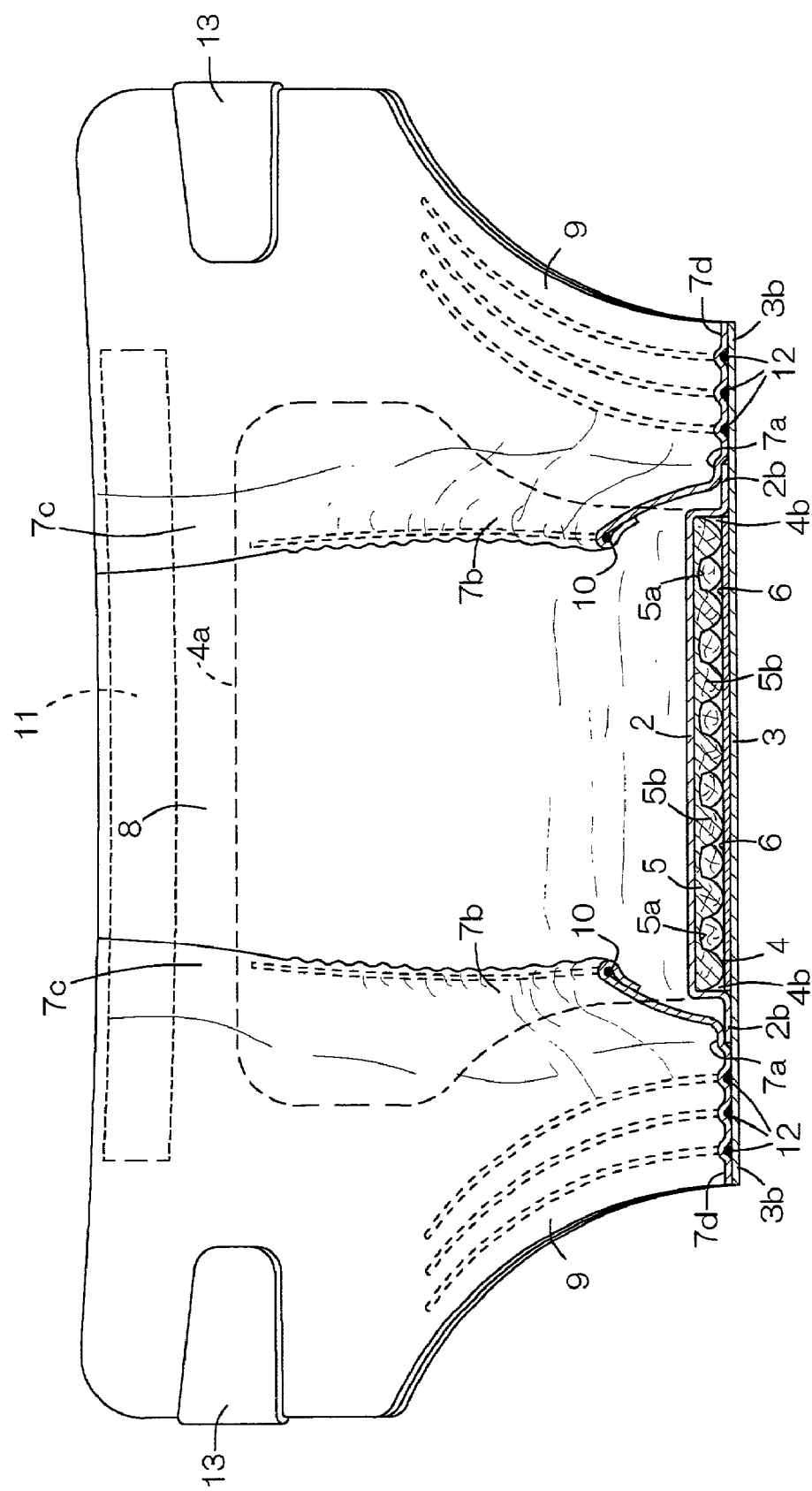
FIG. 4 is sectional view taken along a line IV—IV in FIG. 1.

FIG. 1 a partially cutaway perspective view showing a diaper 1 as viewed from the side of a topsheet 2, FIG. 2 is a perspective view of a liquid-absorbent panel 4 as its first and second sub-panels 5, 6 have been separated from each other, FIG. 3 is sectional view taken along a line III—III in FIG. 1 and FIG. 4 is a sectional view taken along a line IV—IV in FIG. 1. In FIG. 1, a transverse direction is indicated by an arrow X and a longitudinal direction is indicated by an arrow Y. Expression "inner surfaces" of the top- and backsheets 2, 3 used herein should be understood to be the surfaces thereof facing the panel 4 and expression "outer surfaces" of these sheets 2, 3 should be understood to be those not facing the panel 4.

A diaper 1 comprises a liquid-pervious topsheet 2, a liquid-impervious backsheet 3 and the liquid-absorbent panel 4 disposed between these two sheets 2, 3. In addition, the diaper 1 comprises a pair of substantially liquid-impervious leak-barrier cuffs 7.

In the longitudinal direction, the diaper 1 is composed of a front waist region 20, a rear waist region 22 and a crotch region 21 extending between these waist regions 20, 22. The diaper 1 further includes a pair of end flaps 8 extending in the transverse direction along respective longitudinal ends of the front and rear waist regions 20, 22 and a pair of side flaps 9 extending in the longitudinal direction along transversely opposite side edges of the diaper 1. In the crotch region 21, side flaps 9 curve inward transversely of the diaper so as to describe substantially circular arcs.

The panel 4 presents an hourglass-shape which is relatively large in the longitudinal direction and contoured by longitudinally opposite ends 4a extending in the transversal direction and transversely opposite side edges 4b extending in the longitudinal direction. The panel 4 is entirely covered with and joined to a tissue (not shown) and then joined to inner surfaces of the top- and backsheets 2, 3 with the tissue lying therebetween.

The panel 4 comprises a first fibrous assembly sub-panel 5 having a compressive restoring elasticity and a substantially flat second fibrous assembly sub-panel 6. In the panel 4, the first sub-panel 5 faces the topsheet 2 and the second sub-panel 6 underlies the first sub-panel 5.

The first sub-panel 5 has a substantially flat portion 5a, a plurality of protuberant portions 5b embossed toward the second sub-panel 6 and a plurality of wall portions 5c embossed from the flat region 5a toward the second sub-panel 6.

Figure 5:
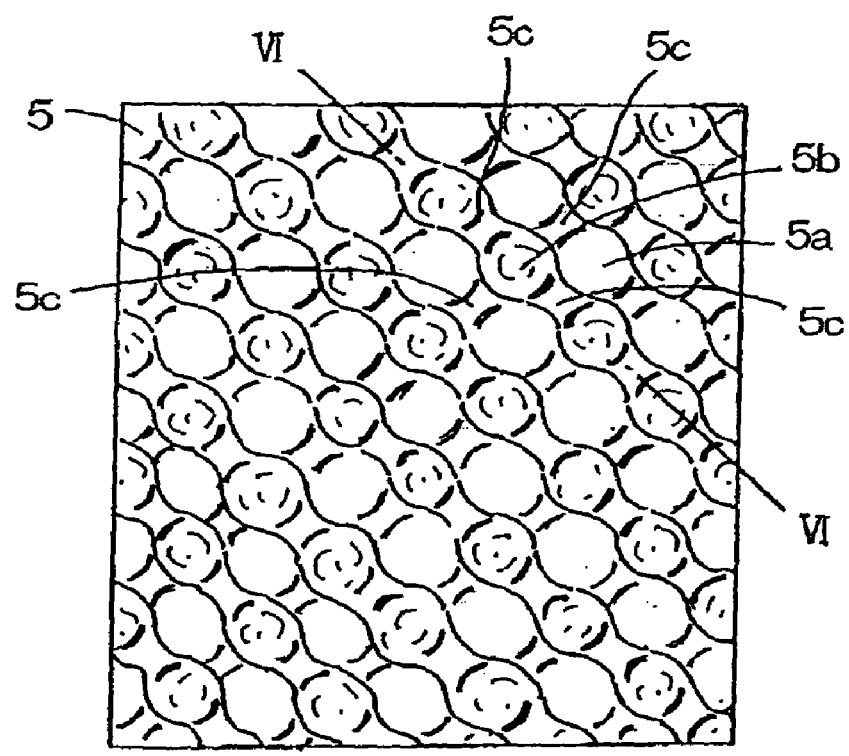
FIG. 5 is a partial top view of the first sub-panel of the invention.
Figure 6:
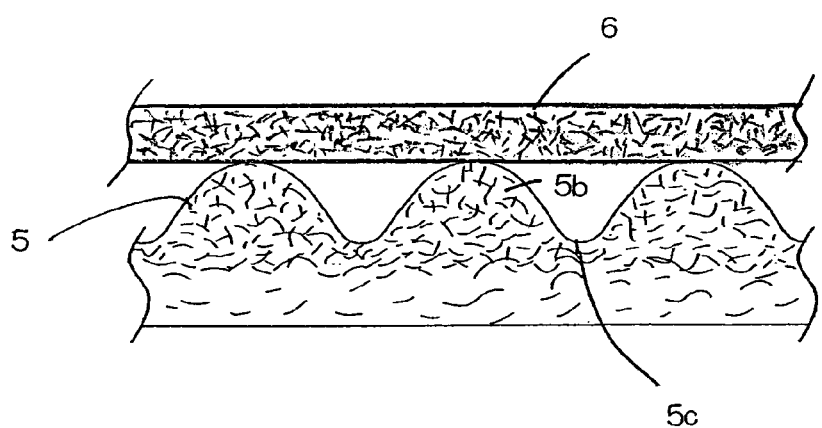
FIG. 6 is a sectional view taken along line VI—VI in FIG 5.

In the first sub-panel 5, the protuberant portions 5b bear against the second sub-panel 6 and the flat portion 5a as well as the wall portions 5c are spaced upward from the second sub-panel 6 by a given dimension. The protuberant portions 5b are substantially spindle-shaped. Each wall portions 5c connect One pair of the adjacent protuberant portions 5b to each other (as best seen in FIGS. 5–6). The first sub-panel 5 has is a fiber density progressively increasing toward the second sub-panel 6.

In the first sub-panel 5, the liquid ingredients such as urine or loose passage having been absorbed in the given area of the flat portion 5a rapidly spread in this flat portion 5a. In the first sub-panel 5, a fiber density of the flat portion 5a is lower than a fiber density of the protuberant portions 5b and the wall portions 5c and therefore a capillary effect in the protuberant portions 5b as well as in the wall portions 5c is higher than a capillary effect in the flat portion 5a. In this way, the body fluids can smoothly transfer from the flat portion 5a toward the protuberant portions 5b and the wall portions 5c.

In the first sub-panel 5, the body fluids can transfer from one protuberant portion 5b to another protuberant portion 5b via the wall portions 5c so as to promote the body fluids to spread in the first sub-panel 5 over its entire area since the protuberant portions 5b are connected one with another by the wall portions 5c.

A fiber density of the second sub-panel 6 is higher that of the first sub-panel 5. In the panel 4, a capillary effect in the second sub-panel 6 is sufficiently higher than that in the first sub-panel 5 to promote the body fluids to transfer from the protuberant portions 5b toward the second sub-panel 6. In the panel 4, the first sub-panel 5 bears against the second panel 6 only at the protuberant portions 5b, so it is more difficult for the body fluids once having been retained in the second sub-panel 6 to flow back to the first sub-panel 5 than in the panel 4 of which the first sub-panel 5 bears over its entire area against the second sub-panel 6.

In the first sub-panel 5, the flat region 5a preferably has a fiber density in a range of 0.03–0.10 g/cm$^3$, the protuberant portions 5b as well as the wall portions 5c preferably have a fiber density in a range of 0.05 –0.15 g/cm$^3$. The second sub-panel 6 preferably has a fiber density in a range of 0.10–0.50 g/cm$^3$.

If the flat region 5a has a fiber density less than 0.03 g/cm$^3$, a body fluid absorbing function of the flat portion 5a would decrease and the first panel 5 could not sufficiently absorb-the body fluids, resulting in that the body fluids would partially stay on the topsheet 2. If the flat region 5a has a fiber density exceeding 0.10 g/cm$^3$, on the contrary, the body fluids would be retained in the flat portion 5a and could not smoothly transfer from the flat region 5a to the protuberant portions 5b and the wall portions 5c.

If the protuberant portions 5b and the wall portions 5c have a fiber density less than 0.05 g/cm$^3$, a body fluid absorbing function of the flat portion 5a would decrease and the body fluids would be retained in and the body fluids could not transfer from the flat portion 5a to the protuberant portions 5b as well as to the wall portions 5c, resulting in that the body fluids would partially stay in the flat region 5a.

If the protuberant portions 5b have a fiber density exceeding 0.15 g/cm$^3$, on the contrary, it would be impossible to ensure a desired difference between the fiber density of the protuberant portions 5b and the fiber density of the second sub-panel 6, i.e., a fiber density gradient between the protuberant portions 5b and the second sub-panel 6. Necessarily, the body fluids could not smoothly transfer from the protuberant portions 5b to the second sub-panel 6. This is true when the second sub-panel 6 has a fiber density less than 0.10 g/cm$^3$.

If the second sub-panel 6 has a fiber density exceeding 0.50 g/cm$^3$, a stiffness of the second sub-panel 6 would increase and uncomfortably irritate the wearer's skin.

The first sub-panel 5 is formed of thermoplastic synthetic resin fiber treated to become hydrophilic. It is also possible to form the first sub-panel 5 using mixed fiber composed of hydrophilic synthetic resin fiber mixed with cellulose fiber.

In the embodiment according to which the first sub-panel 5 contains cellulose fiber, a weight ratio of the cellulose fiber to the first sub-panel 5 is preferably less than 30%. If this weight ratio of the cellulose fiber to the first sub-panel 5 exceeds 30%, a compressive restoring elasticity of the first sub-panel 5 would decrease and, with a disadvantageous consequence, the protuberant portions 5a of the first sub-panel 5 once having been compressed by the wearer's body pressure could not restore the initial thickness thereof. As a result, the flat portion 5b and the wall portions 5c of the first sub-panel 5 would remain bearing against the second sub-panel 6.

The second sub-panel 6 is formed of cellulose fiber. It is also possible to form the second sub-panel 6 using mixed fiber composed of cellulose fiber mixed with hydrophilic synthetic resin fiber. In the embodiment according to which the second panel 6 contains the synthetic resin fiber, a weight ratio of the synthetic resin fiber to the second sub-panel is preferably less than 50%. If the weight ratio of the synthetic resin fiber to the second sub-panel 6 exceeds 50%, a body fluid absorbing function of the second panel 6 would decrease and, in such case, it is concerned that the body fluids might easily leak from the second sub-panel 6.

The second sub-panel 6 may contain therein fibrous or granular super-absorptive polymer. The polymer may be selected from a group consisting of starch-based polymer, cellulose-based polymer and synthetic polymer. In the embodiment according to which the second sub-panel 6 contains super-absorptive polymer, a weight ratio of the super-absorptive polymer to the second sub-panel 6 is preferably less than 50%. If the weight ratio of the super-absorptive polymer to the second panel 6 exceeds 50%, the super-absorptive polymer would be swollen to form gel block as the polymer absorbs the body fluids and the body fluids once having been absorbed in the second sub-panel 6 would be prevented from spreading.

The thermoplastic synthetic resin fiber may be selected from a group consisting of polyolefine-based fiber such as polypropylene or polyethylene fiber, polyester-based fiber such as polyethylene terephthalate or polybutylene terephthalate fiber, polyamide-based fiber such as nylon 66 or nylon 6, or acryl-based fiber. The synthetic resin fiber may be selected from a group consisting of core-sheath type or side-by-side type conjugated fiber of polyethylene/polypropylene or polyethylene/polyester.

The cellulose fiber may be selected from a group consisting of fluff pulp, rayon, acetate or cupra fiber.

The leak-barrier cuffs 7 are provided on the side flaps 9 and extend in the longitudinal direction. The leak-barrier cuffs 7 respectively have fixed edge regions 7a extending immediately outside the respective side edges 4b of the panel 4, free side regions 7b normally biased to rise on the topsheet 2 and longitudinally opposite fixed both end regions 7c collapsed inward transversely of the diaper 1 and fixed in such collapsed state. The leak-barrier cuffs 7 further have the outermost lateral regions 7d extending from the respective fixed edge regions 7a outward transversely of the diaper 1. Elastic members 10 extending in the longitudinal direction are attached under tension to the respective free edge regions 7b so that the free edge regions 7b partially cover the respective elastic members 10.

The end flaps 8 respectively have ribbon-like elastic members 11 operatively associated with a waist-hole attached under tension thereto so as to extend in the transverse direction. In the crotch region 21, the side flaps 9 respectively have a plurality of elastic members 12 operatively associated with a pair of leg-holes attached thereto so as to extend in the longitudinal direction.

In the end flaps 8, longitudinal end regions 2a of the topsheet 2 as well as longitudinal end regions 3a of the backsheet 3 extend longitudinally outward beyond the longitudinal ends 4a of the panel 4 and these end regions 2a, 3a are put flat and joined together, as seen in FIG. 3. The elastic members 11 operatively associated with the waist-hole are disposed between the longitudinal end regions 2a of the topsheet 2 and the longitudinal end regions 3a of the backsheet 3 and joined to these end portions 2a, 3a. The fixed both end regions 7c of the respective leak-barrier cuffs 7 are joined to the longitudinally opposite end regions 2a of the topsheet 2, respectively.

In the side flaps 8, side edge regions 2b of the topsheet 2 extend transversely outward slightly beyond the side edges 4b of the panel 4 and side edge regions 3b of the backsheet 3 as well as side edge regions 7d of the leak-barrier cuffs 7 further extend transversely outward beyond the side edge regions 2b of the topsheet 2. The side edge regions 2b are disposed between the side edge regions 3b and the side edge regions 7d and joined to these side edge regions 3b, 7d. The side edge regions 3b and the side edge regions 7d extending transversely outward beyond the side edge regions 2b are put flat and bonded to each other. The elastic members 12 operatively associated with the leg-holes are disposed between the side edge regions 3b of the backsheet 3 and the side edge regions 7d of the leak-barrier cuffs 7 and joined to these side edge regions 3b, 7d. The fixed edge regions 7a of the leak-barrier cuffs 7 are joined to the side edge regions 2b of the topsheet 2.

In the rear waist region 22, the side flaps 9 are respectively provided with tape fasteners 13 extending inward in the transverse direction. The tape fasteners 13 respectively have proximal end regions disposed between the side edge regions 3b of the backsheet 3 and the side edge regions 7d of the leak-barrier cuffs 7 and joined to these side edge regions 3b, 7d. The tape fasteners 13 respectively have free end regions coated with pressure-sensitive adhesive (not shown). In the front waist region 20, the backsheet 3 is provided on its outer surface with a rectangular target tape strip 14 made of a plastic film. The target tape strip 14 serves as a landing zone for the tape fasteners 13.

To wear the diaper 1, the side flaps 9 in the rear waist region 22 may be placed upon the outer side of the side flap 9 in the front waist region 20, then the free end regions of the respective tape fasteners 13 may be anchored on the target tape strip 14 by a means of the pressure-sensitive adhesive to connect the front waist region 20 with the rear waist region 22. Upon connection of the front and rear waist regions 20, 22, the waist-hole and the pair of leg-holes are defined in the diaper 1.

With this diaper 1, the free edge regions 7b of the leak-barrier cuffs 7 rise on the topsheet 2 as the diaper 1 curves in the longitudinal direction with the topsheet 2 inside. The free edge regions 7b thus rising on the topsheet 2 form barriers against bodily discharges and reliably prevent such bodily discharges from leaking beyond the respective side flaps 9.

The topsheet 2 may be formed using a hydrophilic fibrous nonwoven fabric or a plastic film having a plurality of fine apertures. The backsheet 3 may be formed using a hydrophobic fibrous nonwoven fabric, a liquid-impervious plastic film, a two-layered hydrophobic nonwoven fabric, or a composite sheet composed of a hydrophobic fibrous nonwoven fabric laminated with a plastic film. The leak-barrier cuffs 7 may be formed using a hydrophobic fibrous nonwoven fabric.

It is also possible to form the backsheet 3 as well as the leak-barrier cuffs 7 using a composite nonwoven fabric comprising a melt blown fibrous nonwoven fabric having a high water-resistance sandwiched between two layers of spun bond fibrous nonwoven fabric having high strength and flexibility.

The nonwoven fabric may be selected from a group consisting of those obtained by spun lacing, needle punching, melt blowing, thermal bonding, spun bonding, chemical bonding and air-through processes. The component fiber of such nonwoven fabric may be selected from a group consisting of polyolefine-, polyester- and polyamide-fiber, and core-sheath type conjugated fiber or side-by-side type conjugated fiber of polyethylene/polypropylene or polyethylene/polyester.

Joining between the topsheet 2 and the backsheet 3, fixing of the leak-barrier cuffs 7, joining of the panel 4, and attachment of the respective elastic members 10, 11, 12 may be achieved using hot melt adhesive or heat welding technique such as heat-sealing or supersonic-sealing.

This invention is applicable not only to a disposable diaper but also to a sanitary napkin or a liquid-absorbent pad.

The body fluid absorbent wearing article according to this invention is primarily characterized in that the panel is formed by the first fibrous assembly sub-panel and the second fibrous assembly sub-panel. The first fibrous assembly sub-panel has the fiber density progressively increasing as toward the second fibrous assembly sub-panel and the second fibrous assembly sub-panel has the fiber density higher than that of the first fibrous assembly sub-panel. Such a unique arrangement ensures that the body fluids can rapidly transfer from the flat portion toward the protuberant portions of the first fibrous assembly sub-panel and then rapidly transfer to the second fibrous assembly sub-panel. In the panel, only the protuberant portions of the first sub-panel are bear against the second sub-panel so that the body fluids once having been retained in the second sub-panel are prevented from flowing back to the first sub-panel and therefore to the topsheet. In the first fibrous assembly sub-panel, the body fluids discharged onto a given area of the flat portion can rapidly spread over the entire area of the flat portion and therefore over the entire area of the first fibrous assembly sub-panel.

In the embodiment according to which the first fibrous assembly sub-panel is formed with the wall portions each adapted to connect one pair of the adjacent protuberant portions with each other, the body fluids can transfer from one protuberant portion to another protuberant portion, resulting in an improvement of spread of the body fluids in the first fibrous assembly sub-panel.

What is claimed is:

1. A body fluid absorbent wearing article, comprising:
   a liquid-pervious topsheet:
   a liquid-impervious backsheet;
   a liquid-absorbent panel disposed between said topsheet and said backsheet;
   said panel comprising a first fibrous assembly sub-panel lying on a side of said topsheet and having a compressive restoring elasticity, and a substantially flat second fibrous assembly sub-panel underlying said first fibrous assembly sub-panel;
   said first fibrous assembly sub-panel having opposite upper and lower sides, the upper side being adjacent said topsheet, the lower side being further from said topsheet than the upper side, said first fibrous assembly sub-panel comprising on the lower side thereof a substantially flat portion spaced from said second fibrous assembly sub-panel by a first given dimension and a plurality of protuberant portions extending from said flat portion toward said second fibrous assembly panel so as to bear against said second fibrous assembly sub-panel; and
   said first fibrous assembly sub-panel having a fiber density increasing progressively toward said second fibrous assembly sub-panel which has a fiber density higher than that of said first fibrous assembly sub-panel;
   wherein said first fibrous assembly sub-panel has a plurality of wall portions each extending from said flat portion toward said second fibrous assembly sub-panel, being spaced from said second fibrous assembly sub-panel by a second given dimension smaller than said first dimension, and serving to connect one pair of the adjacent protuberant portions with each other.

2. The body fluid absorbent wearing article according to claim 1, wherein said first fibrous assembly sub-panel has a fiber density of 0.03–0.10 $g/cm^3$ in said flat portion and a fiber density of 0.05–0.15 $g/cm^3$ in said protuberant portions as well as in said wall portions, and said second fibrous assembly sub-panel has a fiber density of 0.10–0.50 $g/cm^3$.

* * * * *